United States Patent
Zereshkian

(10) Patent No.: US 9,809,469 B2
(45) Date of Patent: Nov. 7, 2017

(54) SIPHON TRAP DISINFECTION SYSTEM

(71) Applicant: Gholam Hossein Zereshkian, Richmond Hill (CA)

(72) Inventor: Gholam Hossein Zereshkian, Richmond Hill (CA)

(*) Notice: Subject to any disclaimer, the term of this patent is extended or adjusted under 35 U.S.C. 154(b) by 337 days.

(21) Appl. No.: 14/836,716

(22) Filed: Aug. 26, 2015

(65) Prior Publication Data

US 2017/0057846 A1  Mar. 2, 2017

(51) Int. Cl.
| | |
|---|---|
| C02F 1/46 | (2006.01) |
| A61L 2/03 | (2006.01) |
| E03C 1/126 | (2006.01) |
| E03C 1/28 | (2006.01) |
| C02F 103/00 | (2006.01) |

(52) U.S. Cl.
CPC .......... *C02F 1/4606* (2013.01); *A61L 2/035* (2013.01); *E03C 1/126* (2013.01); *E03C 1/28* (2013.01); *A61L 2202/11* (2013.01); *C02F 2103/003* (2013.01); *C02F 2201/4613* (2013.01); *C02F 2201/4615* (2013.01); *C02F 2201/4617* (2013.01); *C02F 2201/46145* (2013.01); *C02F 2307/14* (2013.01)

(58) Field of Classification Search
CPC .............. C02F 1/4606; C02F 2103/003; C02F 2201/4613; C02F 2201/4615; C02F 2201/4617; C02F 2201/46145; C02F 2307/14; C02F 1/46; A61L 2/035; A61L 2202/11; E03C 1/126; E03C 1/28
See application file for complete search history.

(56) References Cited

U.S. PATENT DOCUMENTS

| | | | |
|---|---|---|---|
| 2015/0041410 A1* | 2/2015 | Niksa | C02F 1/4674 210/748.19 |
| 2016/0304365 A1* | 10/2016 | Marshall | C02F 1/4674 |

* cited by examiner

*Primary Examiner* — Walter D. Griffin
*Assistant Examiner* — Cameron J Allen
(74) *Attorney, Agent, or Firm* — Nasser Ashgriz; UIPatent Inc.

(57) ABSTRACT

A siphon trap disinfection unit consisting of a copper/silver electrode coated on inside body of the siphon parallel to each other along the siphon in the area which water normally stands. A water level sensor to generate resistance between two electrodes and an electric controller circuit to generate ions by applying voltage between two electrodes and controlling the amount of current passing through this control circuit to generate enough concentration of copper and silver ion continuously in the water standing area of the siphon trap to remove and deactivate harmful bacteria's in this area.

20 Claims, 3 Drawing Sheets

SIPHON TRAP DISINFECTION SYSTEM

FIELD OF THE INVENTION

The present invention relates generally to a disinfection system for trap waters and more particularly to a disinfection system for siphon traps.

BACKGROUND OF THE INVENTION

Management of health-care is an important part of hospital hygiene and infection control system. One of the most contaminated sections in the hospitals is the trapped water in siphon system in a sink.

The siphon system of the sink has a water trap, which is located underneath of a sink. The water trap is a bent pipe, which come in different shapes, such as a U, S, or J-shaped traps. Once the sink is used, part of the water remains in the bend. The trapped water seals the pipe blocking the back flow of sewer gases (from the drain pipes back into the occupied space of the building).

The sink drain in a hospital room is an active pool of dangerous bacteria living inside a layer of bio-film. This bio-film not only provides a breeding ground for bacteria, it provides a protective cover. The concentration of bacteria in a water trap may be in a range of $10^6$-$10^{10}$ colony forming units per milliliter (CFU/ml). Therefore, sink drains are recognized as one of the main sources for transmission of hospital infections. These resistant pathogenic microorganisms, which can cause nosocomial infection, can be transmitted by direct contact, through the air, or by a variety other vectors.

When the water runs in the sink, bacteria from the drain get carried up into the air above the drain through aerosols, re-contaminating the hands and splashing onto any other surrounding surfaces, easily infecting patients in the ward. Researches have shown extremely high levels of deadly bacteria, such as Pseudomonas and Clostridium, in hospital sinks may cause various infections, such as urinary tract infection, respiratory system infections, dermatitis, soft tissue, bone and joint infections, and gastrointestinal infections. Healthy individuals have a normal general resistance to infection. Patients with an underlying disease, newborn babies, and the elderly have less resistance and may develop an infection.

Currently, hospitals pour strong disinfectants into the drain. This offers a temporary solution, since the organisms in the bio-film are extremely hard to kill. For example, it is estimated that 50% of staphylococcal strains are resistant to all antibiotics currently in use. The regrowth of the bacteria will begin within days or weeks after the treatment.

Other sterilization methods by using ozone have also shown to be an effective method for disinfection system, however, they are irritant and unhealthy for humans. A combination of UV/ozone sterilizer and a sink trap sterilizer has also been described in the art. These devices are used in combination with other traditional devices, such as air-duct sanitizer or floor sanitizer, for the hospital environment sanitation.

The prior art also discloses application of high heat to the drain siphon along with vibration of the drain. The high heat kills the bacteria continuously and the mechanical vibration prevents bio-film formation inside the drain. This method is complex, consumes a high amount of energy, and is expensive.

Other disinfection methods such as superheat and flush, ultraviolet light and hyper chlorination are also suggested for the standing water in siphon trap. Most of these methods have disadvantages in practice, are costly, labor-intensive and require high power consumption.

The present invention uses an electrochemical treatment to disinfect the trapped water. It is well known that ions of heavy metals such as copper or silver are biocidal for many bacteria. For instance, copper-silver ionization has been used destroy bacteria such as Legionella, the bacteria responsible for legionnaire's disease. Generally, copper-silver ionization has been an effective process to control bacteria in water distribution systems. The presence of copper and silver ions destroys the biofilms and slims of the bacteria. Ionization can be an effective process to control bacteria in water distribution systems found in health facilities. In England, copper-silver ionization is successfully applied in about 120 hospitals for the deactivation of Legionella bacteria. In the United States, copper-silver ionization is used for swimming pool water disinfection. Copper-silver is often used to limit disinfection byproducts formation during chlorine disinfection. Copper-silver ionization is not dependent on temperatures. It is active in the entire water system. Copper-silver ionization is also used by water bottling companies and companies that recycle water throughout the United States.

Copper-silver ionization process is brought about by electrolysis. An electric current is created through copper-silver, causing positively charged copper and silver ions to form. Electrically charged copper ions ($Cu^{2+}$) in the water attract particles of opposite polarity, such as bacteria, viruses and fungi. Positively charged copper ions form electrostatic compounds with negatively charged cell walls of microorganisms. These compounds disturb cell wall permeability and cause nutrient uptake to fail. Copper ions penetrate the cell walls and create an entrance for silver ions ($Ag^+$) to penetrate the core of the microorganism. Silver ions bond to various parts of the cell, such as the DNA and RNA, cellular proteins and respiratory enzymes, causing all life support systems in the cell to be immobilized. As a result, there is no more cellular growth or cell division, causing bacteria to no longer multiply and eventually die out. The ions remain active until they are absorbed by a microorganism. The rate at which the ions are released is automatically maintained by a solid-state, microprocessor-based control unit.

SUMMARY OF THE INVENTION

The present invention is a disinfection system for the disinfection of trapped waters based on copper-silver ionization. In particular, the present invention is a siphon trap disinfection unit which destroys microbiological cells in the trapped water of a sink trap. The unit comprises of a siphon sink drain with a water trap, to replace an existing sink trap.

The sink trap of the present invention has two electrodes inside the water trap section of the drain. The electrodes are from a heavy metal, such as a cupper-silver alloy. The trap is also equipped with a sensor system to determine if the water is flowing inside the sink or it is stagnant. If the water is flowing, then there is no need for ionization. If the water is stagnant, then the ionization starts after a set period of time. The ionization continues until the ion concertation reaches a level that is needed to destroy biological cells. However, the system does not have a concentration measurement system. Instead, the concertation level is determined based on the time that a volume of water is ionized. This time is determined based on the volume of the trapped water (which depends on the size of the sink). The device has a control system that can be programed to start and stop the ionization process based on the set times.

Parts of the inner surfaces of the trap are coated with a metal spray coating at the region of the pipe that water gets traps.

In one embodiment of the present invention, the electrodes are formed by metal spray coating a section of the inner surface of the trap. Metal spray coating provides a durable electrode. The spray coating is applied to two isolated areas. It is preferred that the two coated areas face each other. The coating is a compound with 60% to 90% copper and 10% to 40% silver, preferably comprises of 90% copper+10% silver. Each electrode is connected by wires to an electronic controller circuit.

A power supply connected to the electrodes causes the release of ions. Thereby the present invention continuously supplies electronically controlled amount of copper-silver ions to the water in order to control microbial growth. The control system alternates the polarity of the electrodes to allow for a symmetric erosion of two electrodes.

The siphon trap of the present invention supplies a controlled amount of copper and silver ions by controlling the amount of current passing through the system. A control circuit generates ions of copper and silver with enough concentration when it recognizes that there is no water flow. The system stops ions production after a specific time based on the size and the shape of the siphon. This results in a consistent control of the microbial growth in the standing water volume under the sink.

The siphon trap disinfection unit is further equipped with a sensor system to detect the water flow in the siphon. The sensor system determines the flow of water in the sink and existence of the water in the trap. In one embodiment, the sensor system comprises of two metal plates mounted on the upper U-bend. One of the metal plates is mounted in the trap seal in the siphon trap and the second metal plate is placed in the opposite side of the upper U-bend outside of the water standing area of the siphon trap. The plates are mounted parallel to each other by adhering means or through molding. The sensor is connected to the electronic control unit by wires. The resistance between these two electrodes shows, if the water is flowing in the trap or not and generates a low resistance when the water flow exists and high resistance when water flow stops.

The effectivity of copper-silver disinfection depends on a number of factors, including the concentration of copper and silver ions in the water. The required concentration is determined by the water flow, the volume of water in the system, the conductivity of the water and the concentration of microorganisms in the trapped volume. When the water is contaminated or fouling takes place as a consequence of water hardness and quality, there is a decrease in the electrode release, reducing the effectivity of the electrochemical treatment. By using pure silver and pure copper, the supply of copper and silver ions can be regulated separately.

Copper-silver ionization can deactivate microorganisms in slow-running water and still water. Bacteria's are very susceptive to copper-silver ionization. Copper-silver ionization also takes care of bio film. The copper remains within the bio film causes a residual effect. Copper that stays behind in the bio film takes care of these bacteria. When copper and silver ions are added to water constantly, the concentration of bacteria remains low.

The object of the present invention is to provide a siphon trap disinfection unit by using copper-silver ionization to affectively deactivate bacteria and bio films.

It is another object of the present invention to provide a disinfection system, which does not depend on water temperature.

It is another object of the present invention to provide a system with less maintenance. The system is non-corrosive and causes less strain on the distribution system.

It is another advantage of the present invention to provide a cost effective, easy to use and low maintenance disinfection system.

Another object of the present device to provide for a longer lasting disinfection system. The deactivation rate of copper-silver ionization is lower than that of ozone or UV. Therefore, a benefit of copper-silver ionization is that ions remain in the water for a long period of time. This causes long-term disinfection and protection from recontamination.

Other objects, features, and advantages of the present invention will be readily appreciated from the following description. The description makes reference to the accompanying drawings, which are provided for illustration of the preferred embodiment. However, such embodiments do not represent the full scope of the present invention.

BRIEF DESCRIPTION OF THE DRAWINGS

Embodiments herein will hereinafter be described in conjunction with the appended drawings provided to illustrate and not to limit the scope of the claims, wherein like designations denote like elements, and in which:

DETAILED DESCRIPTION OF PREFERRED EMBODIMENTS

Figure 1:
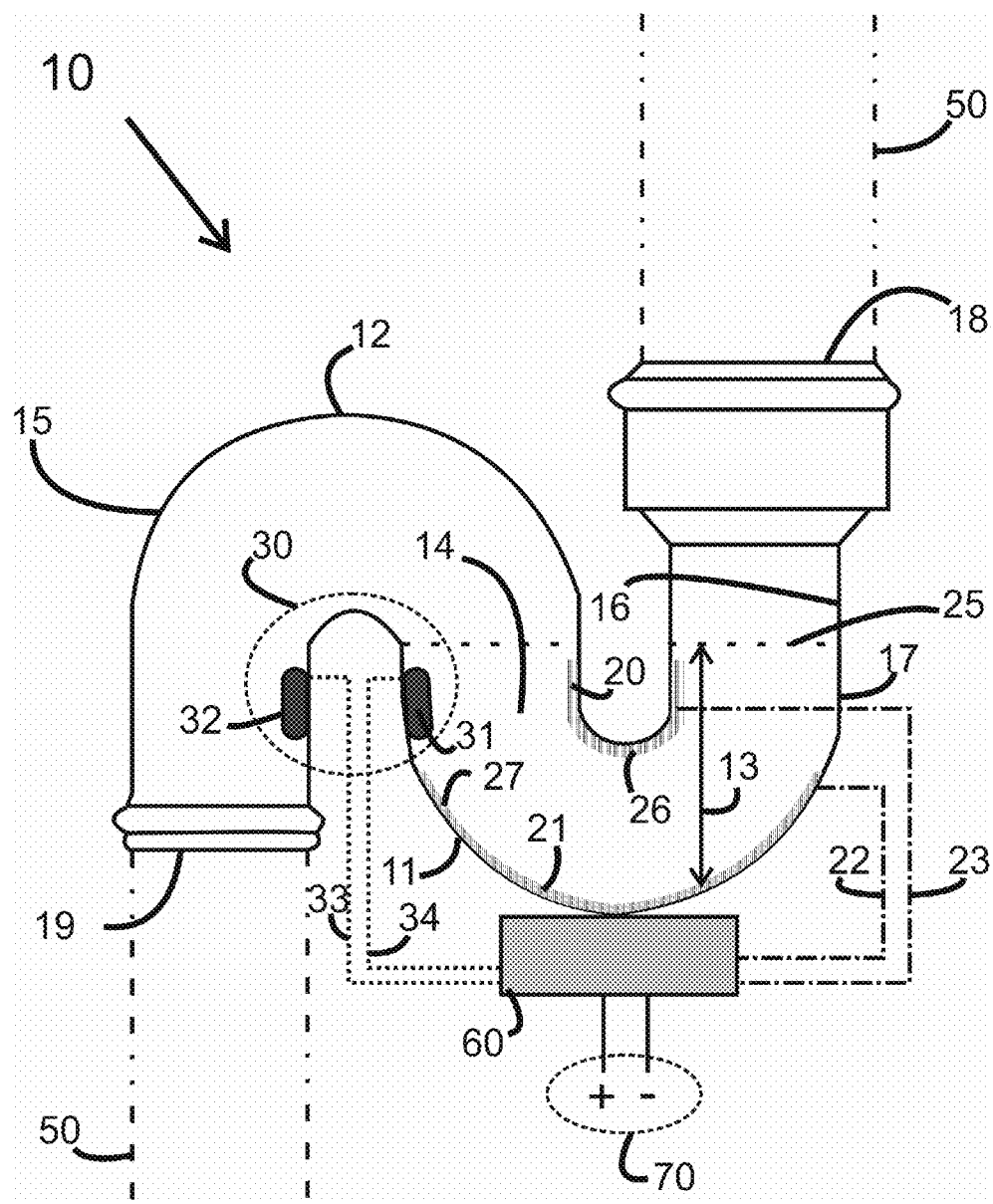
FIG. 1 shows a schematic diagram of the present invention.

One embodiment of the present disinfection device is shown in FIG. 1. A sink trap 10 is installed under a sink and connected to the sink drain 50. The sink trap can be of any design and can be of any material, e.g., plastic or metal. FIG. 1 shows a S-shaped pipe 15 having a lower U-bend 11, an upper U-bend 12, an inside wall 16, an outside wall 17, an inlet 18 and an outlet 19. The S-shaped pipe 15 is connected to the drain channel 50 from its inlet 18 and to the sink drain from its outlet 19. A small amount of water 25 becomes trapped in the lower U-bend 11. The trapped water with a volume of 14 and a height 13 blocks the back flow of gases from the drain to the open sink area. The trap seal depth 13 is typically 1.5 to 2 inches and not more than 4 inches according to some authorities. Bacteria may grow in this trapped water 25, if it remains stagnant for a period of time. The present sink trap is equipped with an ionization system to destroy any micro-biological cells in this trapped water. To achieve this, a first electrode 20 and a second electrode 21 are attached to the inner surfaces 16 of the trapped volume region 14.

In the preferred embodiment of the present device, the electrodes are metal spray coated on two areas 20-21 on the inner surface 16. Spray coating provides very strong electrodes that can last longer and is more resistive to corrosion. The electrodes are made of a specific metal alloy.

The electrodes are preferably made of copper-silver alloy. An alloy of 60-90% copper and 40-10% silver is a good alloy to disinfect water. A preferred ratio of 90% copper+ 10% silver is shown to be very effective to destroy microbiological cells. However, other electrodes, such as titanium electrodes with mixed oxide coatings based on iridium and/or ruthenium oxide, and doped diamond electrodes can also be used. In addition, the electrodes can be of the same material or different materials. However, it is preferred to made the electrodes from the same material, and alternate the polarity on them. This allows that the two electrodes lose mass as the same rate.

Again as shown in FIG. 1, a control unit 60 electronically controls the electrochemical treatment of the trapped water. The control system alternatively changes the polarity on the electrodes—one time one electrode is anode and the next time the other electrode is anode. The sensor system 30 (sensor plates 31-32) sense the flow of water in the drain channel 50. A power source 70 provides power to the device 10.

The two coating areas 20-21 act as the electrodes for the electrochemical treatment to deposit the specific amount of ions into the trapped water 25. Each electrode 20-21 has an exposed area 26-27 and being connected by wires 22-23 to a control unit 60. The control unit 60 results in a current flow through the electrodes 20-21 and causes the release of metal ions into the trapped water 25. The control unit 60 is mounted to the outside wall 17 of the sink.

In another embodiment of the same invention, the coated electrodes are replaced with plate electrodes (not shown). At least two plate electrodes are installed to the inner surfaces of the drain. The plate electrodes generate the electric field needed to deposit the specific amount of ions into the trapped water. Each electrode has an exposed area and is connected by wires to a control unit. The control unit provides applied voltage to the electrode plates and causes the release of ions. The control unit is mounted to the outside wall of the lower bend by an adhesive means.

The siphon trap disinfection unit 10 is further equipped with a water flow sensor 30 to detect the water flow in the siphon. The sensor unit 30 comprises of two plates 31-32 mounted on the inner wall 16 of the lower U-bend 11 and the upper U-bend 12. Plates 31 and 32 are electrically connected through an ohm meter. The resistance between the two plates changes when there is water between them or not. If the water flows inside the siphon, the resistance is low, and if there is no water, the resistance is high. Therefore, the sensor unit 30 determines if there is water flow or not. The sensor unit 30 senses the trapped water and determines how long the trapped water has been stagnant in the trap. If the water is not flowing, then the trapped water is considered to be stagnant and a timer times the stagnation time. If the water is flowing, then there is no need for ionization, since water is not stagnant. The sensor unit 30 is connected to the control unit 60 by wires 33-34 to determine the ionization period.

Other types of sensors, such as conductive and capacitive level sensors, hydrostatic pressure level sensors, acoustic, laser and can also be used. For instance, a conductive level sensor suitable for conductive liquids such as water can be used as a sensor. Such sensors comprise of stainless steel plates having a ceramic, polyethylene or Teflon-based isolators between them. Conductive sensors use low voltages and currents and have the additional benefit of being solid-state devices and are very simple to install and use.

Figure 2:
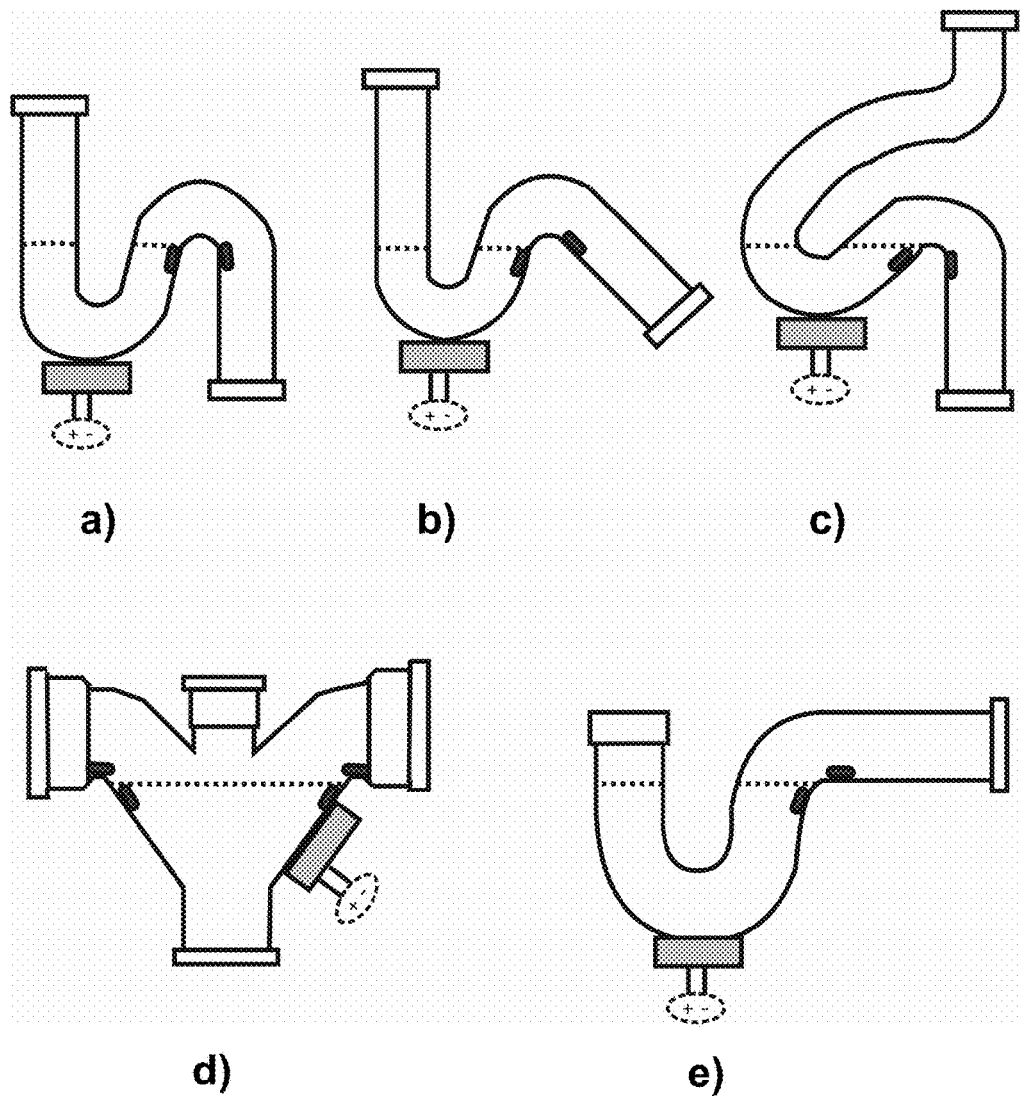
FIG. 2($a$-$e$) show a varieties of embodiments for the present invention.

As shown in FIG. 2(*a-e*), another embodiment of the present invention can have a different design for a siphon trap disinfection unit which provides a constant sterilizing of siphon trap by using the copper-silver ionization. The siphon trap in the present invention as shown in FIG. 2(*a-e*) can have varieties of designs. The siphon trap can be any one of full S-trap (a), ¾ S-trap (b), bag trap (c), Y-trap (d), P-trap (e), U-trap or J-trap. As long as the trap can keep the trapped water in a reservoir, the electrochemical treatment in the trap is possible by the method proposed in the present invention.

Figure 3:
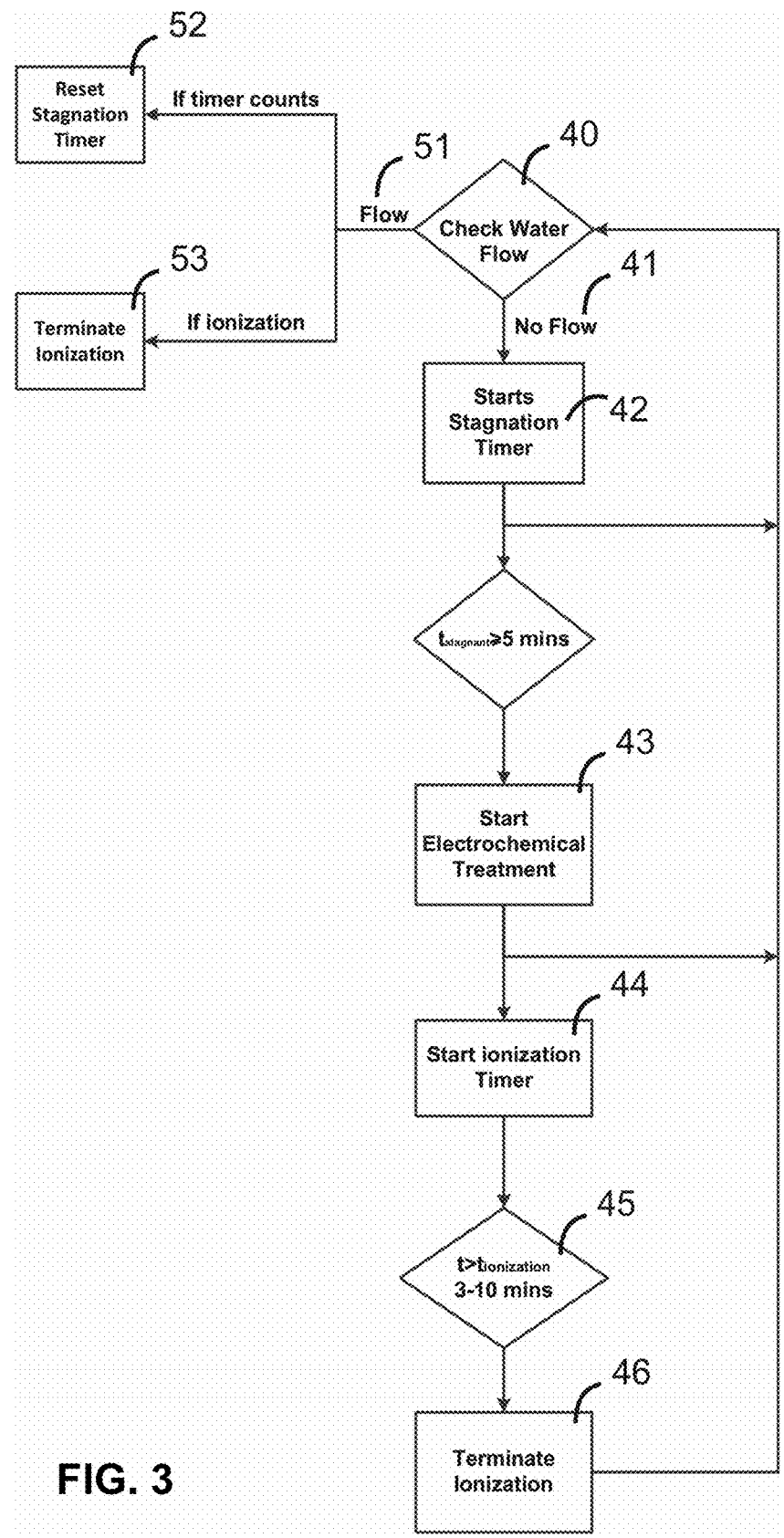
FIG. 3 shows a flow chart of the disinfection process of the present invention.

FIG. 3 shows a block diagram of the process of the present invention. The process in the present invention starts 40 by checking the water flow with the sensor 30. The system continuously checks whether the flow of the water has stopped. When the sensor 30 indicates that there is no flow in the pipes 41, a first timer, stagnation-timer 42, starts timing to determine how long the trapped water is stagnant in the trap. If the water is stagnant for a set period of time, for example five minutes, then the ionization is started 43. The ionization period is determined with a second timer, ionization timer 44, for a set period of time 45, and then stops 46. If the flow starts anytime during the ionization period, the ionization is terminated immediately.

In order to determine the ionization time, first a desired ionization concertation is determined. This desired concentration level is based on the following equation from the sprayed coating electrodes:

$$[\text{Desired concentration } (ppb)] = \frac{aIt}{V} + b$$

where I is the current in mA that is applied to the electrodes, t is time in seconds that the current is applied, V is the volume in liters of the trapped water, and a and b are two constant which are determined based on experimentation. Our tests have shown that the desired concentration can be obtained for the following constants:

a=0.17 b=100

When the concentration in the trapped water reaches to the desired concentration, ionization terminates. Since the concertation is not measured directly, the time required to reach a certain concentration is determined by the above equation. The ionization time based on the above equation is:

$$t = \frac{V}{aI}[\text{Desired concentration } (ppb) - b]$$

The controller is set to apply power for the above ionization time. The system continuously checks to see if the water flows in the pipes or not. If the water does not flow, then the ionization will start again after a pre-set period, preferably five minutes. Therefore, the stagnant water in the trap is ionized every five minutes. If the water is flowing 51, the timer to measure the stagnation time is reset to zero 52, and if the trapped water is being ionized, the ionization is immediately stopped 53. Obviously, the first and the second timers can be replaces with one timer.

A direct current is applied across the electrodes to stimulate the controlled release of ions. The rate at which the ions are released is automatically maintained by a microprocessor in the control unit. The disinfection process is attributed to the positively charged copper-silver ions that form electrostatic bonds with negatively charged sites on microorganism cell walls. Thereby the present invention supplies electronically controlled amount of copper-silver ions continuously to the water in order to control microbial growth.

If the water flow is detected by the level sensor in any steps of the present invention, the timer restarts or the ionization process is terminates and the water flow checking and timer counting executed again.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

With respect to the above description, it is to be realized that the optimum relationships for the parts of the invention in regard to size, shape, form, materials, function and manner of operation, assembly and use are deemed readily apparent and obvious to those skilled in the art, and all equivalent relationships to those illustrated in the drawings and described in the specification are intended to be encompassed by the present invention.

What is claimed is:

1. A disinfection device for a trapped-liquid comprising:
    a. a drain trap for a liquid flow having an inner surface to trap a volume of said trapped-liquid;
    b. a first electrode and a second electrode attached to the inner surface of said drain trap;
    c. said first and said second electrodes are made of or coated with a metal or a metal alloy capable of generating metal ions to eliminate biological cells;
    d. a power supply to provide a current and a voltage to said electrodes for a period of ionization;
    e. a sensor system installed in the drain trap to sense flow of a liquid through said drain trap;
    f. a timer system to determine the length of a stagnant-time that said trapped-liquid is stagnant in the drain trap; and to determine the length of an ionization-time for said period of ionization; and
    g. a control system to control said period of ionization, and to turn on the power to the electrodes when a timer system indicates that the trapped-liquid is stagnant for predefined said stagnant-time and turn off the power when the ionization is performed for predefined said ionization-time or when the liquid flows in the drain.

2. The disinfection device of claim 1, wherein said drain trap is any one of a U-trap, a P-trap, a J-trap, a full S-trap, a ¾ S-trap, a bag trap, or a Y-trap.

3. The disinfection device of claim 1, wherein said electrodes are defined in said inner surface of said drain trap by direct spray coating, whereby spray coating is applied in two front facing areas.

4. The disinfection device of claim 1, wherein said electrodes comprise of a copper-silver alloy.

5. The disinfection device of claim 4, wherein said copper-silver alloy comprises of 60-90% copper and 10-40% silver.

6. The disinfection device of claim 1, wherein said first electrode and said second electrode are made from the same material and said control system alternates the polarity between said first and second electrodes.

7. The disinfection device of claim 1, wherein said first electrode and said second electrode are made by different materials.

8. The disinfection device of claim 1, wherein said power supply is a DC battery.

9. The disinfection device of claim 1, wherein said sensor being any one of a conductive sensor, a capacitive sensor, a hydrostatic or a float sensor, a laser based sensor, or an acoustic sensor.

10. The disinfection device of claim 1, wherein said sensor being a conductive sensor comprising of a first and a second conductive plates, wherein the first plate being installed inside the trapped-liquid and the second plate being installed outside of the trapped-liquid, and thereby, the resistance between the two plates determines if the liquid is flowing or not.

11. The disinfection device of claim 1, wherein said ionization-time is 3 to 10 minutes.

12. A method of disinfecting a trapped-liquid in a drain trap having an inner surface, said method comprising steps of;
    a. attaching a first electrode and a second electrode to the inner surface of the drain trap;
    b. attaching said first electrode and said second electrode to a power supply;
    c. coating the first electrode and the second electrode with a metal or a metal alloy capable of generating a metal ion for the ionization of the trapped-liquid;
    d. installing a sensor on the drain trap to sense the flowing of a liquid inside the drain;
    e. turning on the power to the electrodes if the liquid is not flowing for a predefined stagnant-time;
    f. ionizing the trapped-liquid for a predefined ionization-time, and then stopping the ionization, and
    g. repeating steps e. and f.

13. The method of claim 12, wherein said stagnant-time is five minutes.

14. The method of claim 12, wherein said ionization-time is obtained from:

$$t = (\text{predetermined concentration } (ppb) - b)\frac{v}{aI}$$

wherein t is the ionization time in seconds, I is the current in mA that is applied to the electrode, V is the volume of the trapped water in liters, and wherein constants a and b are predetermined based on the size and shape of a drain.

15. The method of claim 14, wherein a=10.7 and b=100.

16. The method of claim 14, wherein said predetermined concentration of ions is 800-1200 ppb of a copper ion in the trapped-liquid.

17. The method of claim 12, wherein said coating is metal spray coating.

18. The method of claim 12, wherein said coating is a metal coating of 90% Cu+10% Ag.

19. The method of claim 12, wherein said predefined ionization-time is 3 to 10 minutes.

20. The method of claim 12, wherein said method further alternating the polarity between said first and said second electrodes.

* * * * *